US00PP22990P2

(12) United States Plant Patent
Hoddy

(10) Patent No.: US PP22,990 P2
(45) Date of Patent: Aug. 28, 2012

(54) APPLE TREE NAMED 'SOUTHFIELD'

(50) Latin Name: *Malus domestica*
Varietal Denomination: Southfield

(75) Inventor: Richard John Raymond Hoddy, Nelson (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/931,861

(22) Filed: Feb. 10, 2011

(51) Int. Cl.
*A01H 5/00* (2006.01)

(52) U.S. Cl. ..... Plt./161

(58) Field of Classification Search ..... Plt./161
See application file for complete search history.

*Primary Examiner* — June Hwu
*Assistant Examiner* — Louanne Krawczewicz Myers
(74) *Attorney, Agent, or Firm* — Greenlee Sullivan P.C.

(57) ABSTRACT

A new and distinct apple variety is described. The variety results from a limb sport found in Nelson, New Zealand. The fruit of the apple tree of this new variety have an attractive appearance, with a high proportion of red coloration and areas of a darker red coloration in the form of a blush. This new variety is also characterised by an early harvest date and has been named 'Southfield'.

6 Drawing Sheets

Genus and species plant named: *Malus domestica.*
Variety Denomination: 'Southfield'.

BACKGROUND OF THE INVENTION

The new plant variety described herein resulted from a spontaneous limb sport mutation of 'Scifresh' (U.S. Plant Pat. No. 13,888). The 'Scifresh' tree containing the limb sport of the new variety was discovered growing in a cultivated area in Nelson, New Zealand. Nelson is located in the North of the South Island of New Zealand; the Nelson region has a temperate climate and is one of the major pipfruit growing regions of New Zealand.

SUMMARY OF THE INVENTION

Under New Zealand growing conditions the 'Southfield' variety is distinguished from other apple varieties due to the following unique characteristics: the amount and intensity of over color of the fruit, and earlier harvest date of fruit in comparison to 'Scifresh'. Asexual reproduction of this new variety by budding and grafting shows that the aforementioned characteristics are true to form and are established and transmitted through succeeding propagation. This is true of buds grafted onto both M9 and MM106 rootstocks; budding and grafting took place in Nelson, New Zealand. Under the New Zealand growing conditions the new variety was able to be distinguished from the parent variety 'Scifresh', and the parents from which 'Scifresh' was derived 'Braeburn' (not patented) and 'Royal Gala' (U.S. Plant Pat. No. 4,121), by the following characteristics:

'Scifresh': 'Southfield' has an earlier harvest season by approximately a week; and a significantly higher proportion of the skin surface is covered by over color, and has darker red blush as opposed to the distinctive 'Scifresh' stripe.

'Braeburn': 'Southfield' has an earlier harvest season by approximately two weeks, smaller fruit size.

'Royal Gala': 'Southfield' has firmer flesh and longer storage life.

BRIEF DESCRIPTION OF PHOTOGRAPHS

The accompanying photographs show typical specimens of the tree, foliage and fruit of the new variety as depicted in colours as nearly true as is reasonably possible to make the same in a colour illustration of this character. The trees in these photographs, from which plant material was removed and photographed, were three years old when observed.

DETAILED DESCRIPTION

Figure 1:
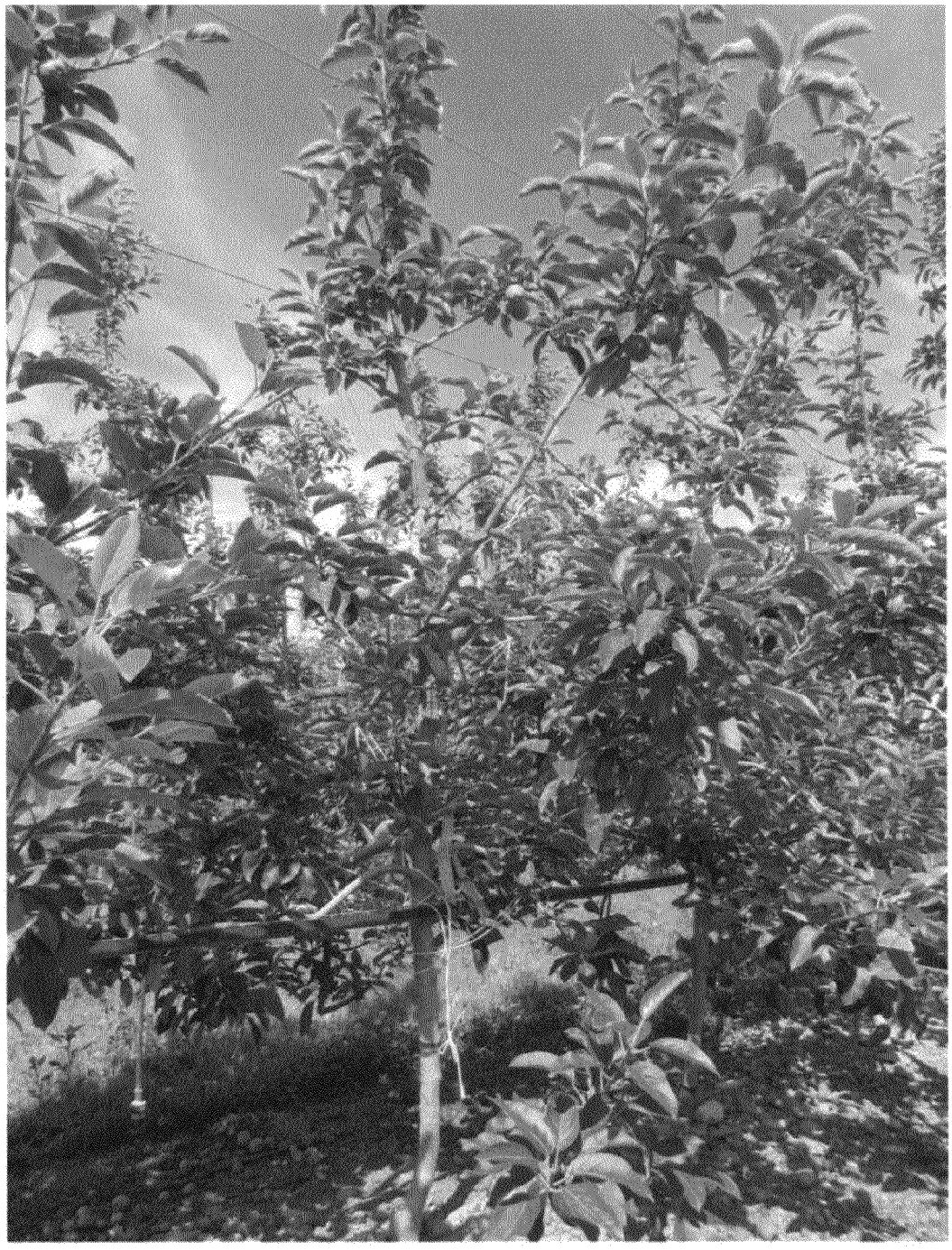
FIG. 1 shows a three year old 'Southfield' scion on M9 rootstock in the field.
Figure 2:
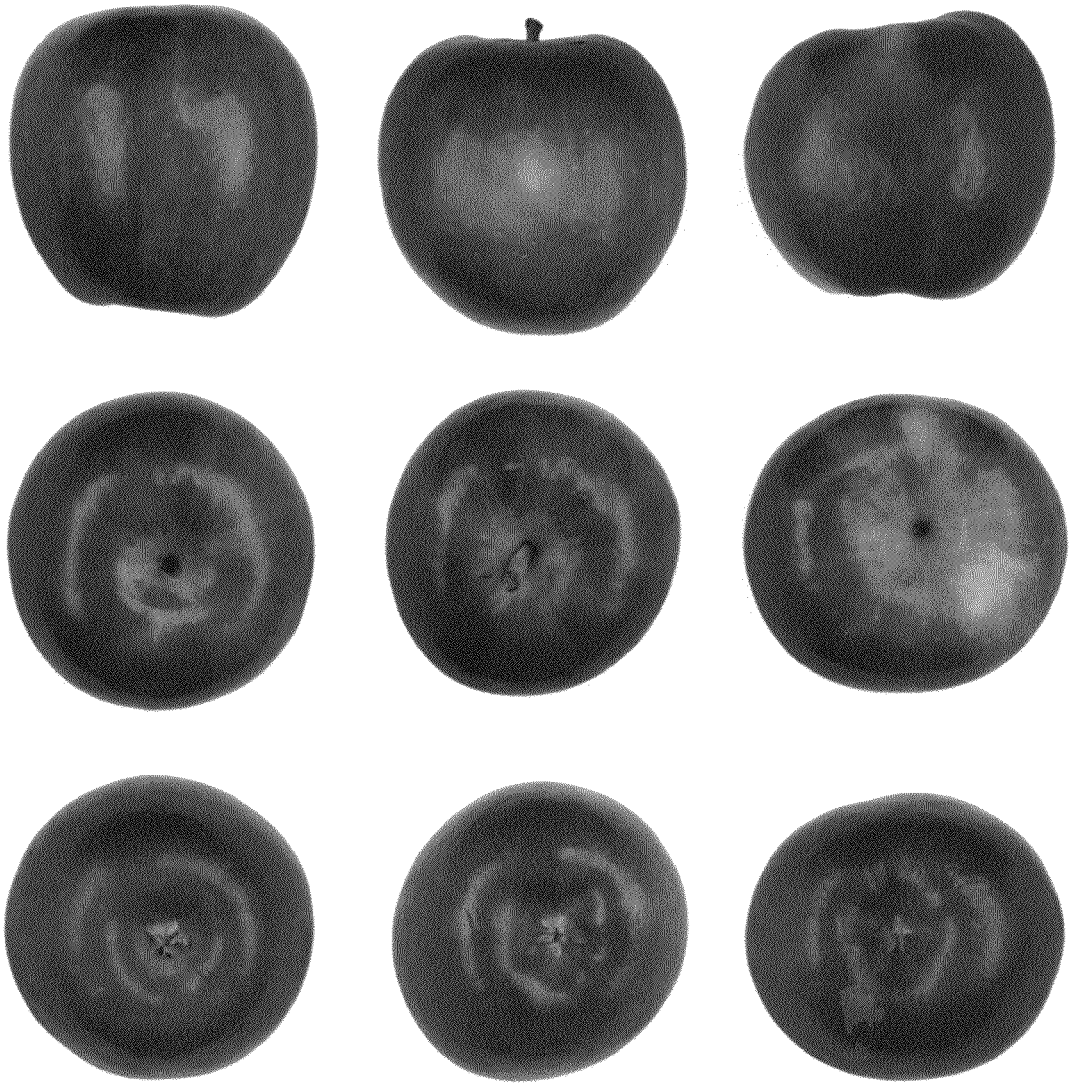
FIG. 2 shows whole 'Southfield' fruit.
Figure 3:
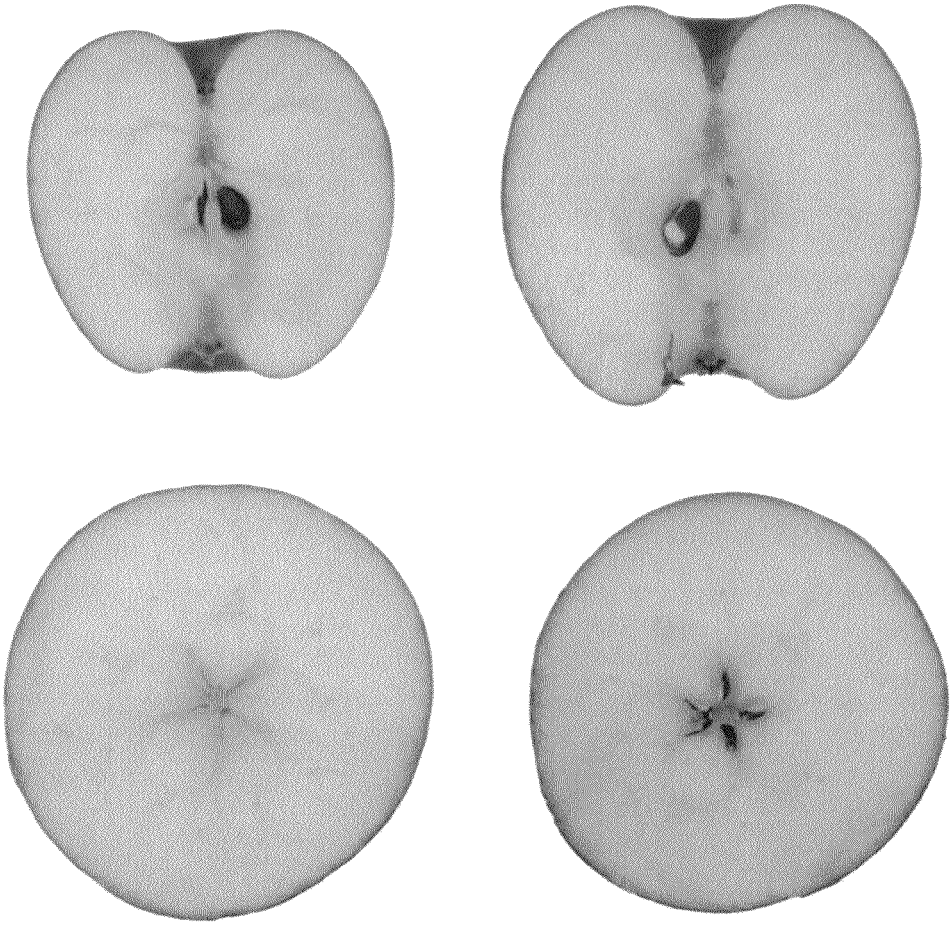
FIG. 3 shows the longitudinal and transverse section of 'Southfield' fruit.
Figure 4:
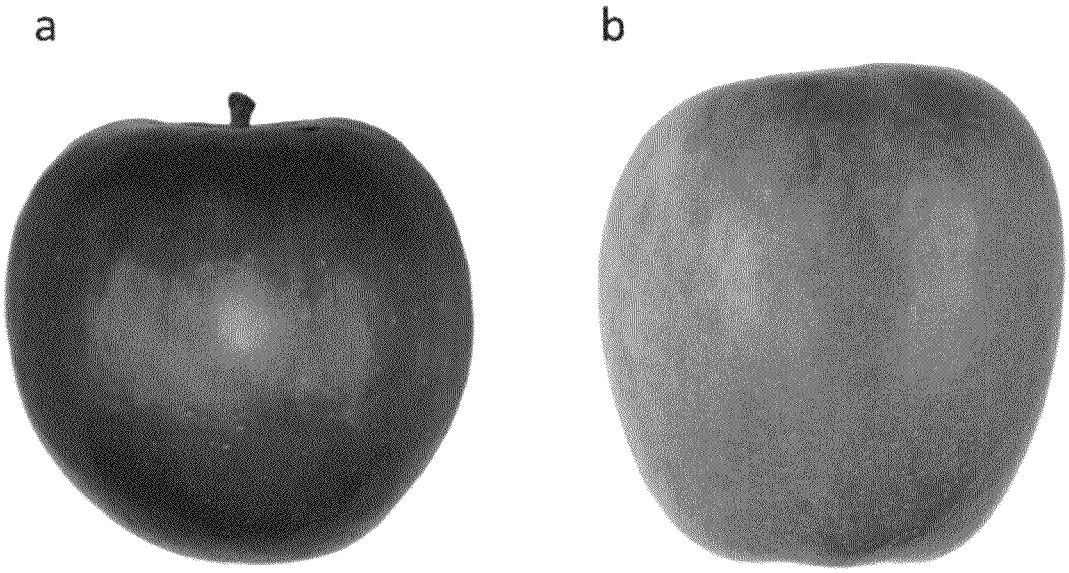
FIG. 4 shows (a) 'Southfield' fruit and (b) 'Scifresh' fruit.
Figure 5:
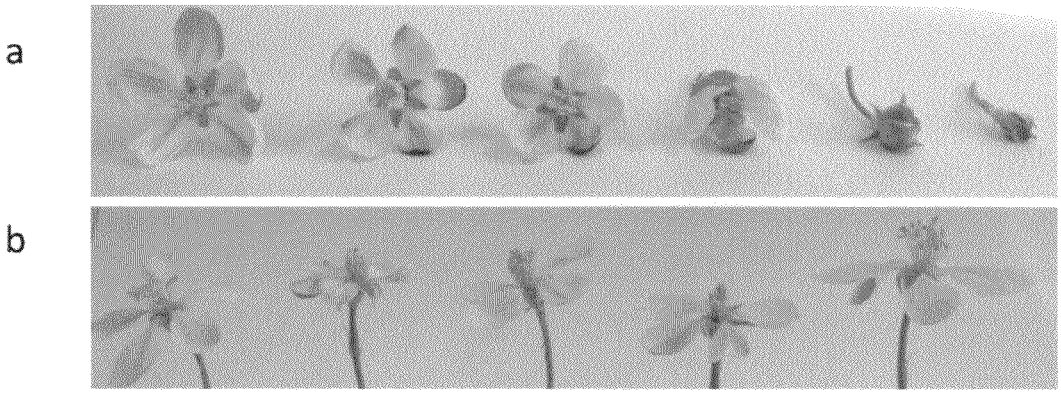
FIG. 5 shows 'Southfield' flowers (a) a range of lower developmental stages, and (b) five fully open flowers.
Figure 6:
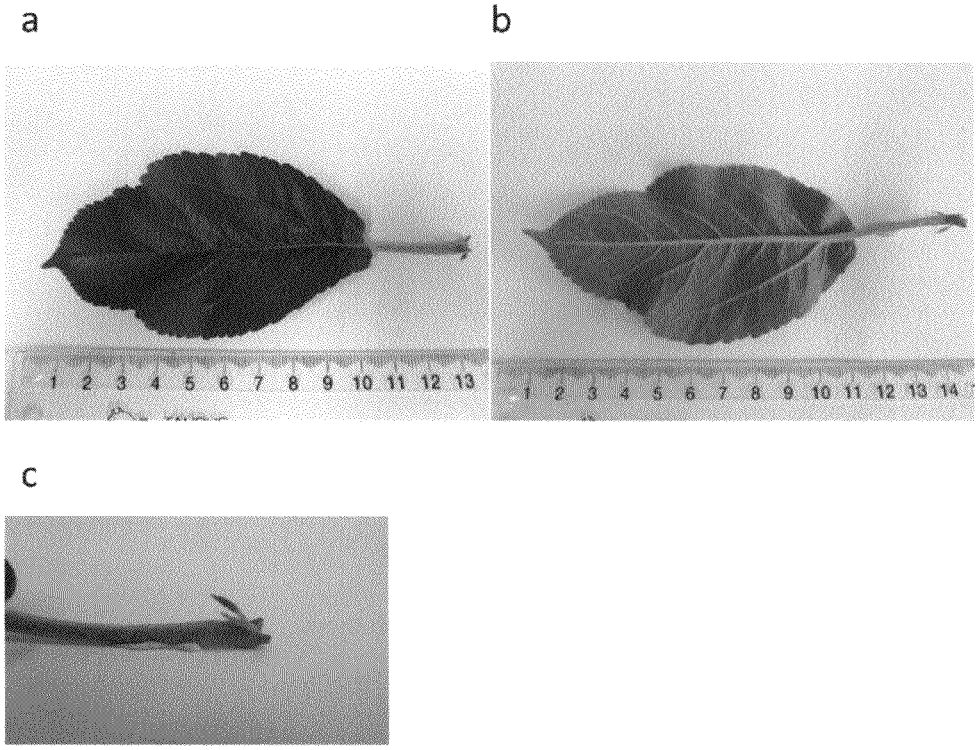
FIG. 6 shows fully expanded 'Southfield' leaves (a) upper side of leaf, (b) lower side of leaf, and (c) petiole and stipules.
Figure 7:
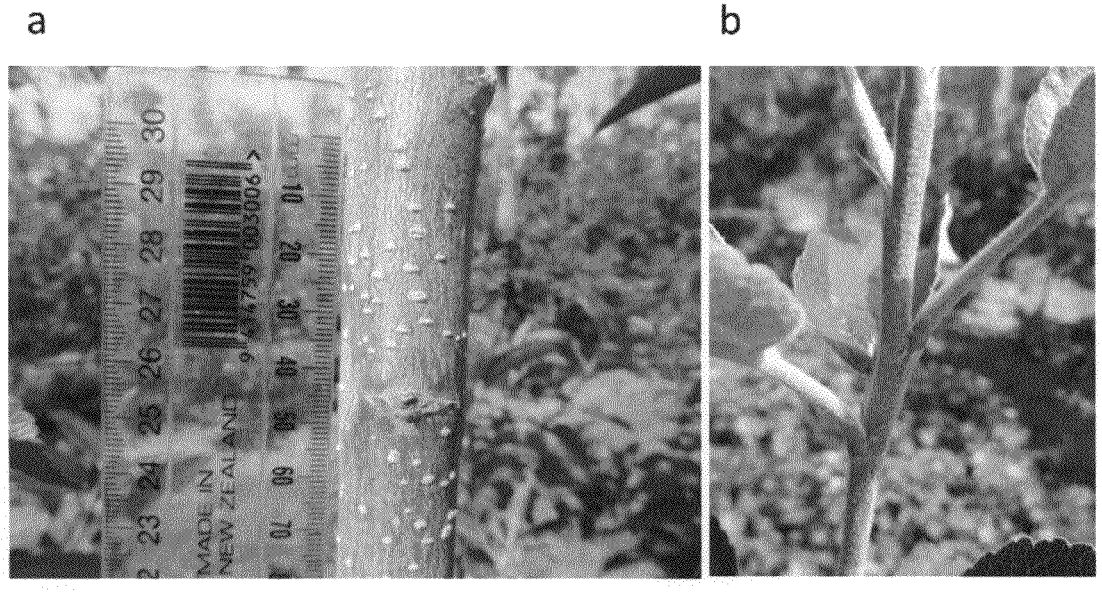
FIG. 7 shows (a) 'Southfield' trunk and (b) spur.

The following is a description of the new variety with color terminology in accordance with The Royal Horticultural Society Colour Charts (R.H.S.C.C.) 2001 edition.

The specimens described were grown at Nelson, New Zealand, except where stated otherwise. The observations were made in the 2009-2010 season on three year old trees, except where stated otherwise.

Tree: Medium size; expressing canopy architecture with a natural tendency for a hierarchy of branching from basitonic to acrotonic, as scaffold branches arrayed around a dominant vertical axis; bearing predominantly on spurs; medium-low vigour on M9 rootstock, managed under standard orchard practice.

Trunk: Color observations were taken from the middle third of the trunk, between 1 and 1.5 m from ground level, on 15 Dec. 2010, under direct sunlight. The background color was near greyed-orange R.H.S.C.C. 166 C with slightly raised sections with an over color of near greyed-white R.H.S.C.C. 156 B. The bark had a moderately rough texture. The average trunk diameter was 15.7 mm measured 200 mm above the graft union on 2 year old trees in Havelock North, New Zealand.

Lenticels: The trunk had a moderate number of raised lenticels. They were divided evenly between slightly larger and smaller lenticels; the smaller were an average of 1.5 mm long by 1 mm wide while the slightly larger were an average of 2.5 mm long by 1 mm wide, lenticels were evenly distributed with an average of three per $cm^2$ and roughly elliptical in shape. The coloration was a mixture of near greyed-white R.H.S.C.C. 156 B and near greyed white R.H.S.C.C. 156 C. Spurs had a moderate number of very slightly raised lenticels in the small range and similarly colored.

Spurs: The coloration is near greyed-orange R.H.S.C.C. 177 A and smooth with a very weak pubescence.

Leaves: The leaves examined were fully expanded and harvested from three year old trees on 15 Dec. 2010. The leaves had an average length of 112 mm and average width of 57 mm at the widest point. The overall shape was moderately to slightly elliptic. The upper side of the blade was near green R.H.S.C.C. N134 A and moderately glossy. The underside was between near yellow-green R.H.S.C.C. 147 C and 148 B with weak pubescence, the reticulate venation coloration was near yellow green R.H.S.C.C. 148 B on both upper and underside. The two sides of the blade were concavely upwardly curving, the basal shape was obtuse and moderately asymmetric, the apex ranged from cuspidate to acuminate though all were acute. The margin of the leaves is irregularly crenate.

Petiole: The average length of the petioles examined was 36 mm, with an average width at the widest point of 3 mm. The coloration of the exposed side of the petiole was near green R.H.S.C.C. 139 D, with a very narrow, approximately 0.5 mm, and of near red 53 B running the length of it. The sides of the petiole were colored near yellow-green R.H.S.C.C. 146 C. The underside of the petioles examined ranged in coloration from near yellow-green R.H.S.C.C. 148 D in the darker areas and 145 C in the lightest areas. There were also very narrow bands with an average length of 2.2 mm randomly dispersed running lengthways with a color of near red R.H.S.C.C. 53 B. The petiole also had weak pubescence; this was weakest on the exposed side. The end of the petiole was colored near red R.H.S.C.C. 53 B.

Stipule: The leaves of 'Southfield' had two filiform stipules each, which were attached at the base of the petiole and angled up the petiole. The average length of the stipules on the leaves examined was 5 mm and the average width was 1 mm. The shape was very elongated elliptic and the coloration of the upper side was near green R.H.S.C.C. N134 A, and less glossy than the blade though unlike the upper surface of the blade they also had a weak pubescence. The color of the underside of the stipules was near yellow-green R.H.S.C.C. 147 B. At the very tip of most of the stipules is a dot of near red R.H.S.C.C. 53 B on both the upper and under sides.

Flowers: Examined from a 480 mm long spur consisting of 210 mm of last season's growth and 190 mm from the year before. Observations were from open flowers unless otherwise stated. The color of the blossom at balloon stage was near red purple R.H.S.C.C. 63 A through B as approaching the basal end of the petal to near white R.H.S.C.C. N155 A through B. The diameter of the open flower was approximately 34.6 mm, the petals were not touching, and there were five flowers per cluster. Bud burst was recorded at 22 August, followed by full bloom at 25 September, and then petal fall at 20 October. The flowers had no observable fragrance.

Petals: Five petals per flower with a shape of slightly elongated elliptic to obovate, average length 16.1 mm, and average width 11.6 mm; with a rounded to slightly truncate apex, a symmetrically attenuate to shortly attenuate base and repand margins. Upper surface coloration was near white R.H.S.C.C. N155 A through B with near red purple R.H.S.C.C. 68 A through C colouration in the veins with faint coloring between the veins in some areas of some petals. Lower surface coloration was near white R.H.S.C.C. N 155 A through B with near red purple R.H.S.C.C. 68 D in veins, some had bands of near red purple R.H.S.C.C. 67 B-C.

Stamen: An average of between 15 to 20 per flower, filaments were near white R.H.S.C.C. 155 D and 6.5 mm long. The dorsi fixed anthers were an average of 2.5 mm long by 1.5 mm wide and coloration near yellow R.H.S.C.C. 11C. Pollen has not been observed to date.

Carpel: Consisted of an inferior ovary, average length 4.5 mm long by 3 mm wide, exterior coloration near yellow green R.H.S.C.C. 148 C. Style, average 8.5 mm long, near yellow green R.H.S.C.C. 145 B; and stigma average 0.9 mm in diameter and near yellow green R.H.S.C.C. 151 C.

Pedicel: Average length 19.8 mm with an average diameter of 1.8 mm, color near yellow green R.H.S.C.C. 146 D and near grey brown R.H.S.C.C. 199 C in places.

Sepals: Five sepals per flower with a shape of moderately elongated triangle. Average 7.7 mm long by 4.7 mm wide. Color range between near yellow green R.H.S.C.C. 144 D and 146 D, on both the upper and lower surfaces, with orange red 34 A at tips.

Fruit: Examined after several months in storage. Fruit were harvested on 16 March in Nelson, New Zealand, five days earlier than nearby 'Scifresh'.

Crop load: Has not been observed to be significantly different to 'Scifresh'. Current standard orchard practice in New Zealand for 'Scifresh' is to thin fruit, depending on growing conditions and intended market, to between approximately 6 to 10 fruit per $cm^2$ TCA (trunk cross sectional area). The typical harvest window for 'Scifresh' under normal New Zealand environmental and management conditions commences in the second week of March and concludes 3-4 weeks later. Growers would normally conduct 3-4 successive selective harvests of fruit based on preferred fruit maturity parameters to optimise post-harvest quality. The harvest window for the candidate variety while commencing earlier, has been observed to be of a similar duration, requiring a similar number of sequential harvests to optimise fruit quality and maximise recovery of yield.

Size: Small to medium; average width, 70 mm; average height 67 mm; average weight, 165 g.

Shape: Ranges from short globose to conical with a medium flat taper; symmetrical in side view.

Skin: Smooth bloom of skin, absent; greasiness of skin, slight; cracking tendency of skin; absent; thickness, medium; background color, near yellow-green R.H.S.C.C. 154D; lenticels, small.

Over color: Approximately 95-98% of skin surface; near red R.H.S.C.C. 46B; with a blush of darker red near R.S.S.C.C. 53A; low amount of russet around stem cavity.

Eye basin: Average width approximately 27 mm, average depth approximately 5.6 mm.

Stalk cavity: Average width approximately 27 mm, average depth approximately 12.5 mm.

Flesh: Firm, juicy and crisp; colored near yellow-white R.H.S.C.C. 158A.

Flesh texture: Medium grained; measured flesh firmness was an average of 8.8 kgf.

Flavour: Medium sweetness; medium acidity; aroma, rich. Average soluble solids 14.3 percent. Observations to date indicate that 'Southfield' does not differ significantly from the original variety 'Scifresh' in terms of titratable acidity, soluble solids, and firmness. It is expected that measurements for this variety will fall within the averaged typical ranges observed at harvest maturity for 'Scifresh' which in New Zealand have been observed to be: titratable acidity 0.55-0.7 percent; soluble solids 12-14 percent and firmness 8.0-9.8 kgf. These factors can be all affected by climate, season, and cultural factors.

Sinus: Closed.

Seeds: Five locules; one to two seeds per locule; medium seed size, 9 mm long, 5 mm wide; color greyed orange near R.H.S.C.C. 175A; moderately asymmetric ovate in shape.

Use: Dessert.

Keeping quality: Excellent.

Winter hardiness and drought tolerance: Tree hardiness has not been observed for the candidate, the New Zealand cool temperate climate does not result in severe weather conditions. However, production of 'Scifresh' (the variety from which 'Southfield' is derived) is well established in Washington State, USA and has not been observed to be susceptible to winter damage under those conditions.

Pest and disease tolerance/susceptibility: 'Southfield' has not been observed to be any more or less tolerant or susceptible to any pests or diseases than 'Scifresh' (the variety from which 'Southfield' is derived) in the areas of New Zealand in which it has been trialed.

The invention claimed is:

1. A new and distinct apple tree substantially as illustrated and described herein.

* * * * *